United States Patent [19]

Marin Moga

[11] 4,072,758
[45] Feb. 7, 1978

[54] COMPOSITIONS AND METHODS FOR EFFECTING GLUCOREDUCTION

[75] Inventor: Antonio Carmelo Marin Moga, Barcelona, Spain

[73] Assignee: J. Uriach y Cia, S.A., Spain

[21] Appl. No.: 656,070

[22] Filed: Feb. 6, 1976

Related U.S. Application Data

[60] Division of Ser. No. 466,412, May 2, 1974, Pat. No. 3,957,866, which is a continuation of Ser. No. 182,187, Sept. 20, 1971, abandoned.

[30] Foreign Application Priority Data

Sept. 23, 1970 Spain .................................. 384463

[51] Int. Cl.² ............................................ A61K 31/18
[52] U.S. Cl. ..................................................... 424/321
[58] Field of Search ................................. 424/321, 322

[56] References Cited

U.S. PATENT DOCUMENTS

| 3,426,067 | 2/1969 | Weber et al. .................. 424/322 X |
| 3,448,149 | 6/1969 | Aumuller et al. ............. 260/553 DA |

FOREIGN PATENT DOCUMENTS

| 746,505 | 8/1970 | Belgium ...................... 260/553 DA |
| 1,571,292 | 5/1969 | France ......................... 260/553 DA |

*Primary Examiner*—Albert T. Meyers
*Assistant Examiner*—Daren M. Stephens
*Attorney, Agent, or Firm*—Steinberg & Blake

[57] ABSTRACT

The invention relates to the use of the compound N-[4-beta-(o-anisamide-ethyl)-benzenesulphonyl]-N'-cyclopentylcarbamide and pharmaceutically acceptable salts thereof as well as compositions therewith plus a pharmaceutical carrier to effect glucoreduction activity, that is lowering of blood sugar levels, with reduced possibility of platelet aggregation and therefore of myocardial infarction.

4 Claims, No Drawings

COMPOSITIONS AND METHODS FOR EFFECTING GLUCOREDUCTION

CROSS REFERENCE TO RELATED APPLICATIONS

This application is a division of my copending application Ser. No. 466,412, filed May 2, 1974, for "Cyclopentyl Carbamide Derivatives and Process for its Production", now U.S. Pat. No. 3,957,866, which in turn is a continuation in part of Ser. No. 182,187, filed Sept. 20, 1971, for "Cyclopentyl Carbamide Derivatives and Process for its Production", now abandoned.

BACKGROUND OF THE INVENTION

Hypoglycemic agents that can be used orally for reduction of blood sugar levels, such as tolbutamide [1-butyl-3-(p-tolysulfonyl) urea] have been used for many years. However, the known agents suffer from numerous disadvantages and new agents having this effect have been sought.

SUMMARY OF THE INVENTION

Generally speaking, the present invention relates to N-[4-beta-(o-anisamide-ethyl)-benzenesulphonyl]-N'-cyclopentylcarbamide and its pharmaceutically acceptable salts such as the sodium salt, the potassium salt, etc., to pharmaceutical compositions containing the same, and to the use of this compound and its salts to effect the lowering of blood sugar levels.

The compound of the present invention has the following structural formula:

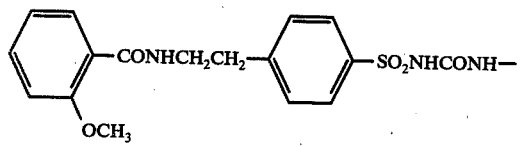

It is accordingly a primary object of the present invention to provide new compositions and the use thereof to effect the lowering of blood sugar levels.

It is another object of the present invention to provide pharmaceutical compositions of N-[4-beta-(o-anisamide-ethyl)-benzenesulphonyl]-N'-cyclopentyl-carbamide and physiologically compatible or pharmaceutically acceptable salts thereof with any pharmaceutically acceptable carrier, particularly a carrier for oral administration.

It is yet a further object of the present invention to provide for the administration of the above compound and its salts to effect the lowering of blood sugar levels.

The compound of the present invention, N-[4-beta-(o-anisamide-ethyl)-benzenesulphonyl]-N'-cyclopentyl-carbamide may also be designated as N-[4-(beta-(2-methoxybenzamide)-ethyl)-benzenesulphonyl]-N'-cyclopentylurea.

This compound of the invention has the effect of providing an effective glucoreduction activity, that is the lowering of the blood sugar levels, by stimulating the release of insulin. However, unlike other closely related sulphonylureas, such as N-[4-(beta-(2-methoxybenzamido)-ethyl)-benzenesulphonyl]-N'-cyclohexylurea and N-[4-(beta-(2-methoxy-5-chlorobenzamido)-ethyl)-benzenesulphonyl]-N'-cyclopentylurea, the compound of the present invention gives quickly rise to a sharp increase in insulin output followed by slow diminution thereof. This difference in manner of acting results in much greater possibilities of use of the compound of the present invention to effect the lowering of blood sugar levels than with the other sulphonylureas mentioned above. Thus, whereas the other sulphonylureas have the effect of exhausting and abusing the pancreas so that the pancreas cannot recover between two consecutive doses thereof, the compound of the present invention acts in a manner that permits a safer clinical use than the other two mentioned compounds.

In addition, the compound of the present invention has much less inhibitory action on the heart phosphodiesterase activity so that the use thereof provides a much smaller probability of myocardial infarction incidence than in the case of the use of the other mentioned sulphonylureas.

Furthermore, the compound of the present invention inhibits human platelet aggregation, thus further reducing the possibility of myocardial infarction upon use of the same.

DESCRIPTION OF PREFERRED EMBODIMENTS

The following examples are given to further illustrate the present invention. The scope of the invention is not, however, meant to be limited to the specific details of the examples.

EXAMPLE 1

This example describes a production of N-[beta-(o-anisamide-ethyl)-benzenesulphonyl]-N'-cyclopentyl-carbamide.

46.5 g of 4-(beta-(o-anisamide)-ethyl)-benzenesulphonamide and 19.3 g of finely pulverized anhydrous potassium carbonate are suspended in 1000 ml of anhydrous dioxane. The mixture is heated to 80° C. and subsequently 30.4 of ethyl chloroformate are added dropwise. The temperature is maintained for 12 hours and, after this time has elapsed, a solution of 13.1 g of cyclopentylamine and 10 g. of acetic acid in 10 ml of dioxane are added. The reaction mixture is heated under reflux for 2 hours, after which the dioxane is evaporated under reduced pressure, the residue is dissolved in a solution of 1% ammonium hydroxide and there is separated by filtration the insoluble fraction constituted by a small quantity of 4-(beta-(-anisamide)-ethyl)-benzenesulphonamide which has not been converted to the desired product.

The ammonia solution is clarified with activated carbon and concentrated hydrochloric acid is added thereto up to substantially acid pH, whereupon the crude N-(4-beta-(o-anisamide-ethyl)-benzenesulphonyl-N'-cyclopentylcarbamide precipitates. The product is recrystallized in absolute ethanol. The melting point is 173° – 175° C.

The water soluble sodium or potassium salt may be formed with the corresponding alkali.

A preparation containing the above compound as active substance can be processed into the appropriate dosage unit form with a carrier such as talc, starch, lactose etc. The dosage per unit is 2.5–5.0 mg. The daily dose may vary from 2.5–20 mg per day.

EXAMPLE 2

Tablets are prepared by usual tabletting procedures comprising 2.5 or 5.0 mg. of N-[4-beta-(o-anisamide-ethyl)-benzenesulphonyl]-N'-cyclopentylcarbamide and lactose as pharmaceutical excipient. These tablets can be administered for the purpose of effecting glucoreduction.

EXAMPLE 3

A diabetic patient having high level of blood sugar but who does have functionally active pancreatic beta cells is administered the N-[4-beta-(o-anisamide-ethyl)-benzenesulphonyl]-N'-cyclopentylcarbamide in amounts up to 20 mg per day in the form of tablets each containing 2.5 or 5.0 mg of the compound.
The lowering of blood sugar level is observed.

While the invention has been illustrated in particular with respect to a particular composition for effecting glucoreduction, it is to be understood that variations and modifications can be made.

What is claimed is:

1. Method of effecting glucoreduction in a patient requiring the same, which comprises administering to such patient a glucoreduction effective amount of N-[4-beta-(o-anisamide-ethyl)-benzenesulphonyl]-N'-cyclopentylcarbamide or a pharmaceutically acceptable salt thereof.

2. Method according to claim 1 wherein the mode of administration is oral.

3. Composition for achieving glucoreduction, comprising a pharmaceutical carrier and a glucoreduction effective amount of N-[4-beta-(o-anisamide-ethyl)-benzenesulphonyl]-N'-cyclopentylcarbamide or a pharmaceutically acceptable salt thereof.

4. Composition according to claim 3 wherein said carrier is suitable for oral administration.